US011918280B2

(12) United States Patent
Sherman et al.

(10) Patent No.: US 11,918,280 B2
(45) Date of Patent: Mar. 5, 2024

(54) METHODS AND SYSTEMS TO COMBINE RF ABLATION THERAPY WITH DEVICE NAVIGATION

(71) Applicant: Medtronic Ablation Frontiers LLC, Minneapolis, MN (US)

(72) Inventors: Marshall L. Sherman, Cardiff By The Sea, CA (US); Catherine R. Condie, Shoreview, MN (US); Trenton J. Rehberger, Minneapolis, MN (US); Steven J. Fraasch, Maple Grove, MN (US); Mark T. Stewart, Lino Lakes, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 819 days.

(21) Appl. No.: 16/904,692

(22) Filed: Jun. 18, 2020

(65) Prior Publication Data

US 2020/0315703 A1 Oct. 8, 2020

Related U.S. Application Data

(62) Division of application No. 15/277,404, filed on Sep. 27, 2016, now Pat. No. 10,722,302.

(Continued)

(51) Int. Cl.

*A61B 18/14* (2006.01)
*A61B 5/00* (2006.01)

(Continued)

(52) U.S. Cl.

CPC .......... *A61B 18/1492* (2013.01); *A61B 5/283* (2021.01); *A61B 5/304* (2021.01); *A61B 5/6852* (2013.01); *A61B 18/1233* (2013.01); *A61B 2017/00044* (2013.01); *A61B 2018/0016* (2013.01); *A61B 2018/00357* (2013.01); *A61B 2018/00577* (2013.01); *A61B 2018/00875* (2013.01); *A61B 18/0206* (2013.01); *A61B 2018/0212* (2013.01); *A61B 2018/124* (2013.01); *A61B 2018/128* (2013.01); *A61B 2018/1407* (2013.01);

(Continued)

(58) Field of Classification Search

CPC ...................................................... A61B 5/065

See application file for complete search history.

(56) References Cited

U.S. PATENT DOCUMENTS

| | | | |
|---|---|---|---|
| 5,657,755 | A | 8/1997 | Desai |
| 7,792,563 | B2 | 9/2010 | Cohen et al. |

(Continued)

*Primary Examiner* — Ronald Hupczey, Jr.

(74) *Attorney, Agent, or Firm* — Michael Best & Friedrich LLP

(57) ABSTRACT

Methods and systems for combining ablation therapy with navigation of the ablation device. An ablation system may be configured for use with one of two methods to prevent loss of navigation signals during ablation energy delivery. In the first method, ablation energy signals are filtered from the navigation signal. In the second method, the delivery of ablation energy is sequenced with the delivery of navigation energy such that ablation energy and navigation energy are not delivered at the same time and navigation signals received by the system are time-division multiplexed to reconstruct the navigation signals and determine a location of the device within the patient.

14 Claims, 8 Drawing Sheets

Related U.S. Application Data

(60) Provisional application No. 62/235,777, filed on Oct. 1, 2015.

(51) Int. Cl.

| | |
|---|---|
| ***A61B 5/283*** | (2021.01) |
| ***A61B 5/304*** | (2021.01) |
| ***A61B 17/00*** | (2006.01) |
| ***A61B 18/00*** | (2006.01) |
| ***A61B 18/02*** | (2006.01) |
| ***A61B 18/12*** | (2006.01) |
| ***A61B 34/20*** | (2016.01) |
| ***A61B 90/00*** | (2016.01) |

(52) U.S. Cl.

CPC ................. *A61B 2018/1467* (2013.01); *A61B 2034/2053* (2016.02); *A61B 2090/062* (2016.02)

(56) References Cited

U.S. PATENT DOCUMENTS

| | | | | |
|---|---|---|---|---|
| 9,364,277 | B2 | 6/2016 | Sisken et al. | |
| 2005/0261571 | A1 | 11/2005 | Willis et al. | |
| 2009/0253976 | A1 | 10/2009 | Harlev | |
| 2012/0226271 | A1 | 9/2012 | Callas et al. | |
| 2012/0302869 | A1 | 11/2012 | Koyrakh et al. | |
| 2013/0274582 | A1* | 10/2013 | Afonso | A61B 5/065 600/374 |
| 2014/0364715 | A1 | 12/2014 | Hauck | |
| 2015/0119690 | A1 | 4/2015 | Deno et al. | |
| 2016/0051322 | A1* | 2/2016 | Asirvatham | A61N 1/0551 606/41 |
| 2016/0184004 | A1* | 6/2016 | Hull | A61B 5/287 600/509 |
| 2016/0242667 | A1 | 8/2016 | Fay et al. | |
| 2017/0360498 | A1 | 12/2017 | Davies et al. | |
| 2018/0110554 | A1 | 4/2018 | Zarins et al. | |

* cited by examiner

| On/Off Cycle 1 | | On/Off Cycle 2 | | On/Off Cycle 3 | | On/Off Cycle 4 | | On/Off Cycle 5 | | On/Off Cycle 6 | | On/Off Cycle 7 | |
|---|---|---|---|---|---|---|---|---|---|---|---|---|---|
| On | Off (X Plane) | On | Off (Y Plane) | On | Off (Z Plane) | On | Off (Unipolar Z HF) | On | Off (Bipolar Z HF) | On | Off (Unipolar Z LF) | On | Off (Bipolar Z LF) |
| 1 msec | 7 msec | 1 msec | 7 msec | 1 msec | 7 msec | 1 msec | 7 msec | 1 msec | 7 msec | 1 msec | 7 msec | 1 msec | 7 msec |

*FIG. 7*

| On/Off Cycle 1 | | On/Off Cycle 2 | | On/Off Cycle 3 | | On/Off Cycle 4 | | On/Off Cycle 5 | | On/Off Cycle 6 | | On/Off Cycle 7 | |
|---|---|---|---|---|---|---|---|---|---|---|---|---|---|
| On | Off (X Plane) | On | Off (Y Plane) | On | Off (Z Plane) | On | Off (Unipolar Z & θ HF) | On | Off (Bipolar Z & θ HF) | On | Off (Unipolar Z & θ LF) | On | Off (Bipolar Z & θ LF) |
| 1 msec | 7 msec | 1 msec | 7 msec | 1 msec | 7 msec | 1 msec | 7 msec | 1 msec | 7 msec | 1 msec | 7 msec | 1 msec | 7 msec |

*FIG. 8*

METHODS AND SYSTEMS TO COMBINE RF ABLATION THERAPY WITH DEVICE NAVIGATION

CROSS-REFERENCE TO RELATED APPLICATION

This application is a divisional of U.S. patent application Ser. No. 15/277,404, filed Sep. 27, 2016 and is related to and claims priority to U.S. Provisional Patent Application Ser. No. 62/235,777, filed Oct. 1, 2015, entitled METHODS AND SYSTEMS TO COMBINE RF ABLATION THERAPY WITH DEVICE NAVIGATION, the entirety of which is incorporated herein by reference.

STATEMENT REGARDING FEDERALLY SPONSORED RESEARCH OR DEVELOPMENT n/a

TECHNICAL FIELD

The present invention relates to methods and systems for combining radiofrequency treatment with navigation of the medical device.

BACKGROUND

Cardiac arrhythmias present in the heart disrupt normal rhythm and cardiac efficiency. These arrhythmias can be treated using ablation techniques such as radiofrequency (RF), ultrasound, microwave, pulsed electric field, cryoablation, and other forms of ablation. In the case of ablation techniques that involve the delivery of electrical therapy, a catheter can be used in a multiuse capacity where it serves its primary function of ablation energy delivery, but it can also be used to measure electrograms or aid in location via electrical navigation methods.

However, difficulties arise when attempting to monitor the location of the treatment catheter using navigation programs while the energy delivery is active. For example, RF ablation energy tends to be delivered at a very high level (greater than thirty volts), whereas the navigation signals tend to be used at a very low level (on the order of millivolts). Without apparatus to filter or sequence the navigation signals with respect to the RF ablation energy, the navigation signals are obliterated by the RF energy and are not generally recoverable.

SUMMARY

The present invention advantageously provides methods and a system for methods and a system for the disambiguation of navigation signals from the high-level ablation energy signals. In one embodiment, a system for determining a location of a medical device during a procedure in which ablation energy is delivered to a tissue area within a patient may include a medical device including at least one energy delivery electrode and at least one mapping electrode, an ablation energy source in electrical communication with the at least one energy delivery electrode, a navigation system being in communication with the at least one mapping electrode of the medical device, and a switching system in communication with the energy source and the navigation system, the switching system being configured to selectively place the at least one energy delivery electrode in communication with the energy source or the navigation system.

In one embodiment, the switching system may include a switch between the energy source and the navigation system, an energy detector in communication with the energy generator, the energy detector being configured to determine whether energy is delivered from the energy source to the at least one energy delivery electrode, and a logic apparatus in communication with the energy detector and the switch, the logic apparatus being configured to selectively open and close the switch based on the determination of the energy detector. In one embodiment, the switching system may further include a shunt between the switch and the navigation system.

In one embodiment, wherein the navigation system may further include a plurality of external electrodes and an alternating current source that is configured to deliver alternating current from a plurality of sources to the plurality of external electrodes. In one embodiment, the alternating current source may be configured to deliver alternating current electricity to each of the plurality of sources at a same frequency. In one embodiment, the navigation system may include a processing unit having processing circuitry that is configured to time-division multiplex the frequency for each of an X plane, a Y plane, and a Z plane. In one embodiment, the processing circuitry may be further configured to time-division multiplex voltage signals received from the at least one mapping electrode of the medical device. In one embodiment, the processing circuitry may be further configured to time-division multiplex impedance measurements received from the medical device in each of a unipolar mode and a bipolar mode. In one embodiment, the processing circuitry may be further configured to time-division multiplex impedance measurements received from the medical device at each of a first frequency and a second frequency. In one embodiment, the first frequency may be between approximately 5 kHz and approximately 25 kHz and the second frequency may be between approximately 80 kHz and approximately 120 kHz.

In one embodiment, the navigation system may be configured to determine coordinates of the medical device in a plane when the switching system selectively places the at least one energy delivery electrode in communication with the navigation system.

In one embodiment, the system may further comprise an energy detector in communication with the energy generator, wherein the switching system is configured to place the at least one energy delivery electrode in communication with the navigation system when at least 10 msec elapses without the energy detector detecting energy from the energy source.

In one embodiment, the energy source may produce pulsed electric field energy. In one embodiment, the pulsed electric field energy may be delivered in at least one train of 5-μsec pulses with an off period of at least 5-μsec between pulses, each pulse train including between 60 and 120 pulses.

In one embodiment, a system for determining a location of a medical device within a patient during a procedure in which radiofrequency energy is delivered to a tissue area within a patient may include: a medical device including at least one radiofrequency energy delivery electrode and at least one mapping electrode; a radiofrequency energy source in electrical communication with the at least one radiofrequency energy delivery electrode; and a navigation system being in communication with the at least one mapping electrode of the medical device, the navigation system being configured to determine coordinates of the medical device within the patient, the navigation system including: a plurality of external electrodes; an alternating current source configured to deliver alternating current from a plurality of sources to the plurality of external electrodes at a frequency; and a processing unit having processing circuitry configured to: time-division multiplex the frequency for each of an X plane, a Y plane, and a Z plane; time-division multiplex voltage signals received from the at least one mapping electrode of the mapping device; time-division multiplex impedance measurements received from the medical device in each of a unipolar mode and a bipolar mode; and time-division multiplex impedance measurements received from the medical device at each of a first frequency and a second frequency, the first frequency being between approximately 5 kHz and approximately 25 kHz and the second frequency is between approximately 80 kHz and approximately 120 kHz. The system may further include a switching system in communication with the radiofrequency energy source and the navigation system, the switching system being configured to selectively place the at least one radiofrequency energy delivery electrode in communication with the radiofrequency energy source or the navigation system, the switching system including: a switch between the radiofrequency energy source and the navigation system; a radiofrequency energy detector in communication with the radiofrequency energy generator, the radiofrequency energy detector being configured to determine whether energy is delivered from the radiofrequency energy source to the at least one radiofrequency energy delivery electrode; a logic apparatus in communication with the radiofrequency energy detector and the switch, the logic apparatus being configured to selectively open and close the switch based on the determination of the radiofrequency energy detector; and a shunt between the switch and the navigation system.

In one embodiment, the switching system may be configured to place the at least one energy delivery electrode in communication with the navigation system when at least 10 msec elapses without the energy detector detecting radiofrequency energy from the radiofrequency energy source.

In one embodiment, a method of determining a location of a treatment device during an ablation procedure within a patient may include: delivering ablation energy from an ablation electrode of the treatment device to an area of tissue; delivering navigation energy to a plurality of external patch electrodes from a plurality of navigation energy sources, the navigation energy delivered by each of the plurality of navigation energy sources being a same frequency; transmitting a plurality of voltage signals from a mapping electrode of the medical device to a processing unit, the processing unit time-division multiplexing the voltage signals; and determining a location of the medical device within a patient based on the time-division multiplexed voltage signals.

In one embodiment, the processing unit time-division multiplexes the voltage signals in each of a first plane, a second plane, and a third plane.

In one embodiment, the frequency is a first frequency and the method further includes: transmitting a plurality of impedance signals from the mapping electrode of the medical device to the processing unit when the navigation energy is delivered in unipolar mode, the processing unit time-division multiplexing the impedance signals; and transmitting a plurality of impedance signals from the mapping electrode of the medical device to the processing unit when the navigation energy is delivered in bipolar mode, the processing unit time-division multiplexing the impedance signals. In one embodiment, the frequency is a second frequency greater than the first frequency, and the method may further include: transmitting a plurality of impedance signals from the mapping electrode of the medical device to the processing unit when the navigation energy is delivered in unipolar mode, the processing unit time-division multiplexing the impedance signals; and transmitting a plurality of impedance signals from the mapping electrode of the medical device to the processing unit when the navigation energy is delivered in bipolar mode, the processing unit time-division multiplexing the impedance signals.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 7 shows a first exemplary duty cycle;

FIG. 8 shows a second exemplary duty cycle; and

DETAILED DESCRIPTION

Figure 1:
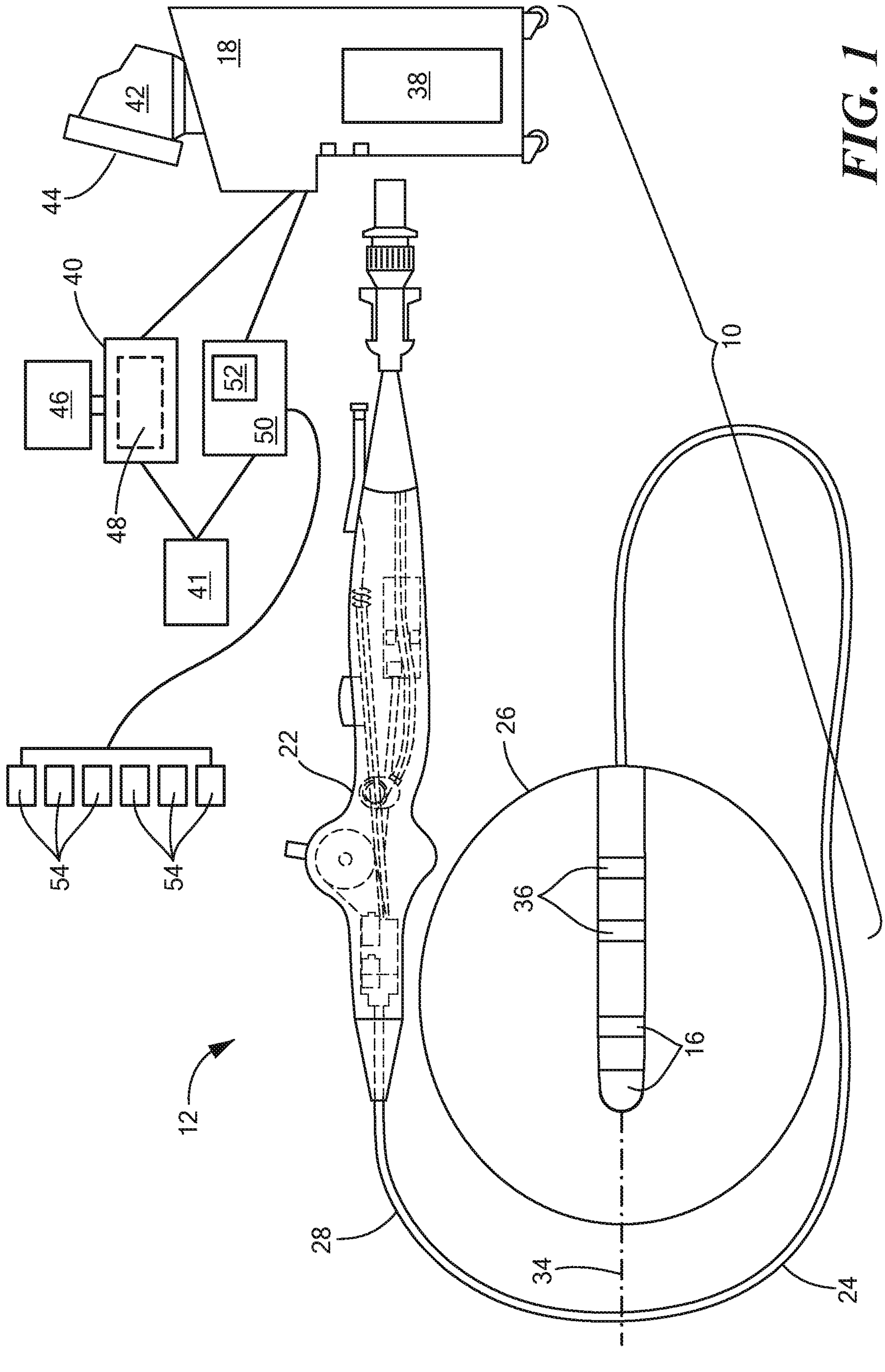
FIG. 1 shows a first exemplary system for treating tissue.
Figure 2:
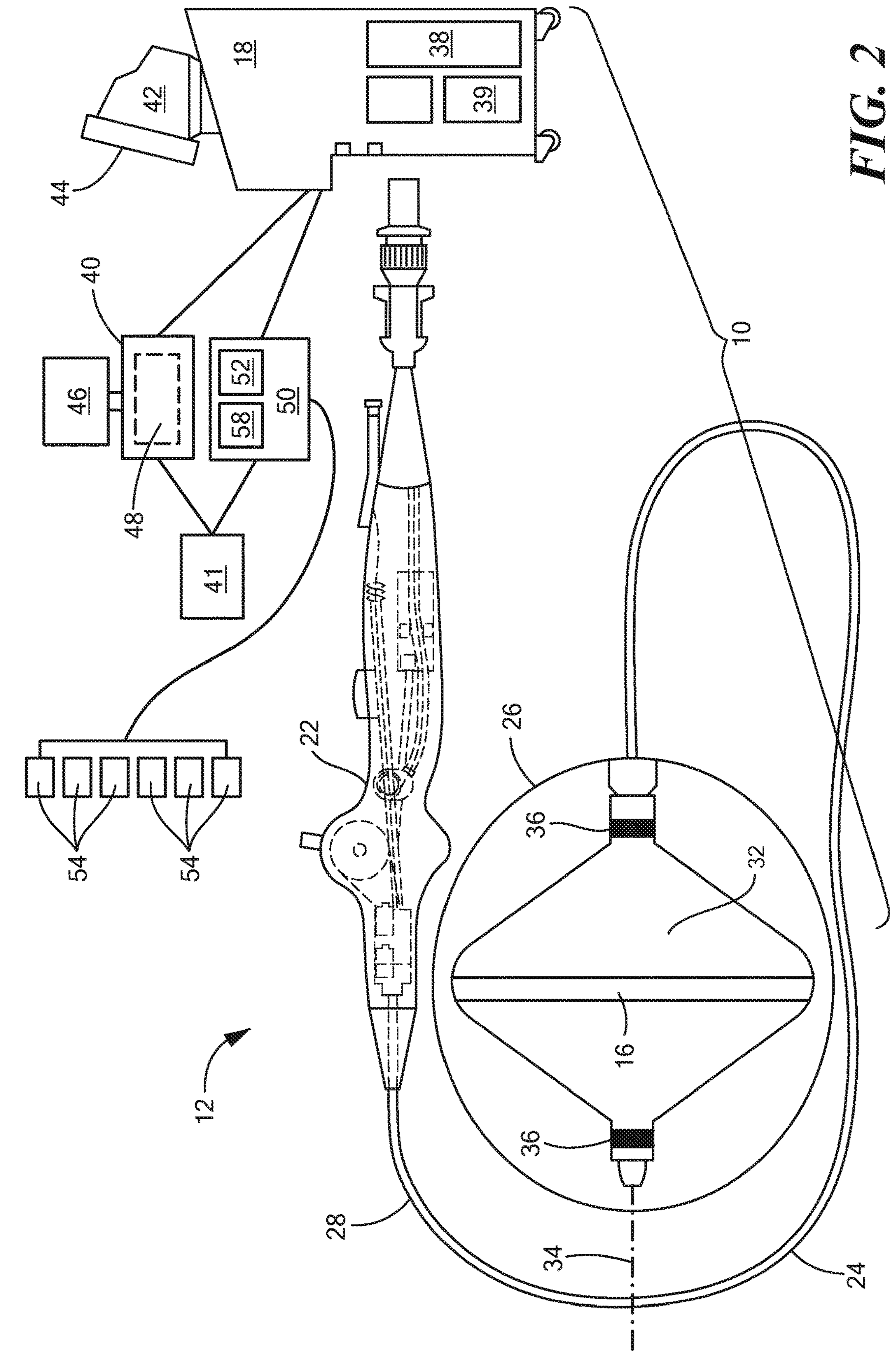
FIG. 2 shows a second exemplary system for treating tissue.
Figure 3:
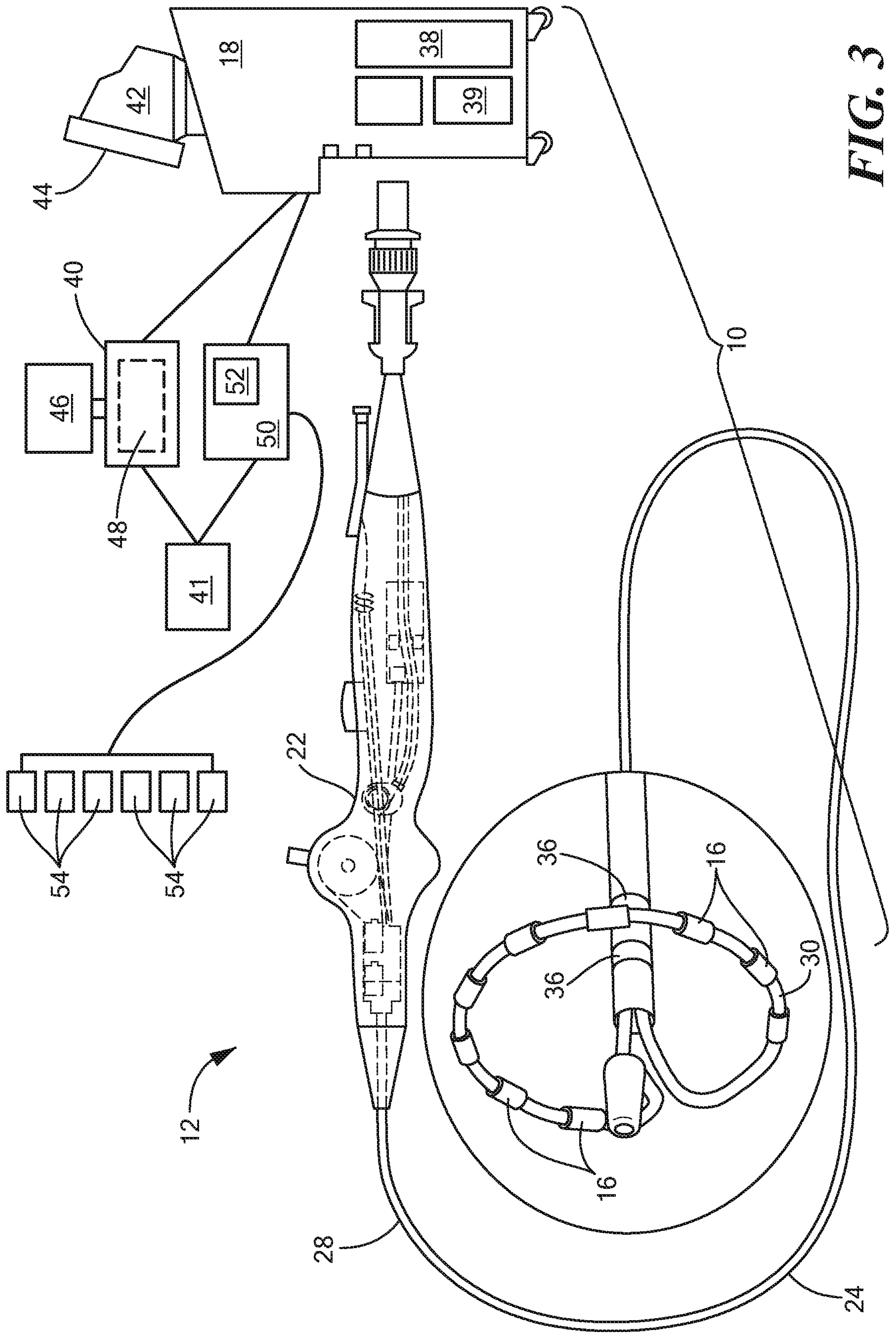
FIG. 3 shows a third exemplary system for treating tissue.

Referring now to FIGS. 1-3, exemplary systems for treating tissue are shown. The system 10 may be used for treating, ablating, and/or mapping one or more target tissue areas. The system 10 may generally include a treatment device 12, such as a treatment catheter, having one or more treatment or therapy electrodes 16 for the delivery of ablation or treatment energy and a console 18 that includes various system controls. The system 10 may be adapted for use with radiofrequency (RF) energy, phased RF energy, and/or pulsed field ablation (PFA) energy (delivered as square and/or sine waves) and may additionally be adapted for ablation or treatment using other energy modalities such as cryoablation and cryotherapy, ultrasound energy, laser energy, microwave energy, hot balloon treatment or ablation, or other modalities or combinations thereof. A description of exemplary PFA energy delivery techniques is described in U.S. Ser. No. 15/228,406, which application is incorporated herein by reference in its entirety.

The treatment device 12 may generally include a handle 22, an elongate body 24 having a distal portion 26 and a proximal portion 28, one or more treatment elements such as non-expandable electrodes 16 (for example, as may be used on a focal catheter), an expandable or non-expandable electrode array (for example, an expandable array having one or more carrier arms 30 bearing a plurality of electrodes 16, as shown in FIG. 3), or an inflatable balloon 32 that may bear a plurality of electrodes (as shown in FIG. 2). Although the balloon 32 is shown in FIG. 2 as having one electrode strip, it will be understood that any number or configuration of electrodes may be used. Further, the treatment device 12 may have a longitudinal axis 34 and one or more mapping electrodes 36.

The treatment device 12 may include one or more lumens. For example, the treatment device 12 may include one or more lumens for electrical wiring, steering elements, or the like. In addition to the treatment of tissue using RF energy, the system 10 may be used for cryotreatment procedures in which tissue is thermally affected by the circulation of a coolant within the treatment element. For example, the one or more treatment elements may include a cryoballoon 32 with a plurality of electrodes 16 for ablating tissue (as shown in FIG. 2), and the device 12 may include one or more mapping electrodes 36. As a non-limiting example, the mapping electrodes 36 may be located on the elongate body 24 proximal the balloon 32. In this case, the treatment device 12 may also include, for example, a fluid injection lumen in fluid communication with a coolant supply reservoir 38 and a coolant recovery lumen in fluid communication with a coolant recovery reservoir or scavenging system. Further, the coolant recovery lumen may be in communication with a vacuum to facilitate removal of fluid from the cryoballoon (for example, expanded coolant). It will be understood, therefore, that reference herein to delivering energy to tissue also includes removing heat from tissue through a cryotreatment procedure.

The console 18 may be in electrical and, if used for cryotreatment, fluid communication with the treatment device 12 and may include one or more fluid (for example, cryotreatment coolant) reservoirs 38, energy generators 40, switching systems 41, and computers 42 with displays 44, and may further include various other displays, screens, user input controls, keyboards, buttons, valves, conduits, connectors, power sources, processors, and computers for adjusting and monitoring system parameters. As used herein, the term "computer" may refer to any programmed or programmable data-processing unit having processing circuitry including a memory and processor, the memory in communication with the processor, the memory having one or more instructions or algorithms that, when executed by the processor, configure the processor to perform the calculations and analyses discussed herein. For example, the data-processing unit may include a smart phone, dedicated internal circuitry, user control device, or the like. As a non-limiting example, the system may include a GENius® Generator (Medtronic, Inc.) as an energy generator 40, but the GENius® Generator may also record data from the device, and therefore also be referred to as a "computer." Further, the energy generator 40 may include one or more displays 46, user input devices, controllers, data storage units, or the like. The computer(s) 42, power generator 40, and/or console 18 may include one or more processing units that are in electrical communication with the one or more electrodes 16, 36 and one or more fluid valves (for example, if the system is configured for cryotreatment). As discussed above, each processing unit 48 may have processing circuitry that includes a memory and processor, with the processing circuitry being configured to receive data from the treatment device 12, process data, and to communicate data to a navigation system 50. Additionally, although the power generator 40 and navigation system 50 are shown as being external to the console 18, these components may alternatively be located within the console 18 and/or integrated with the computer 42 and other components of the console 18.

Figure 4:
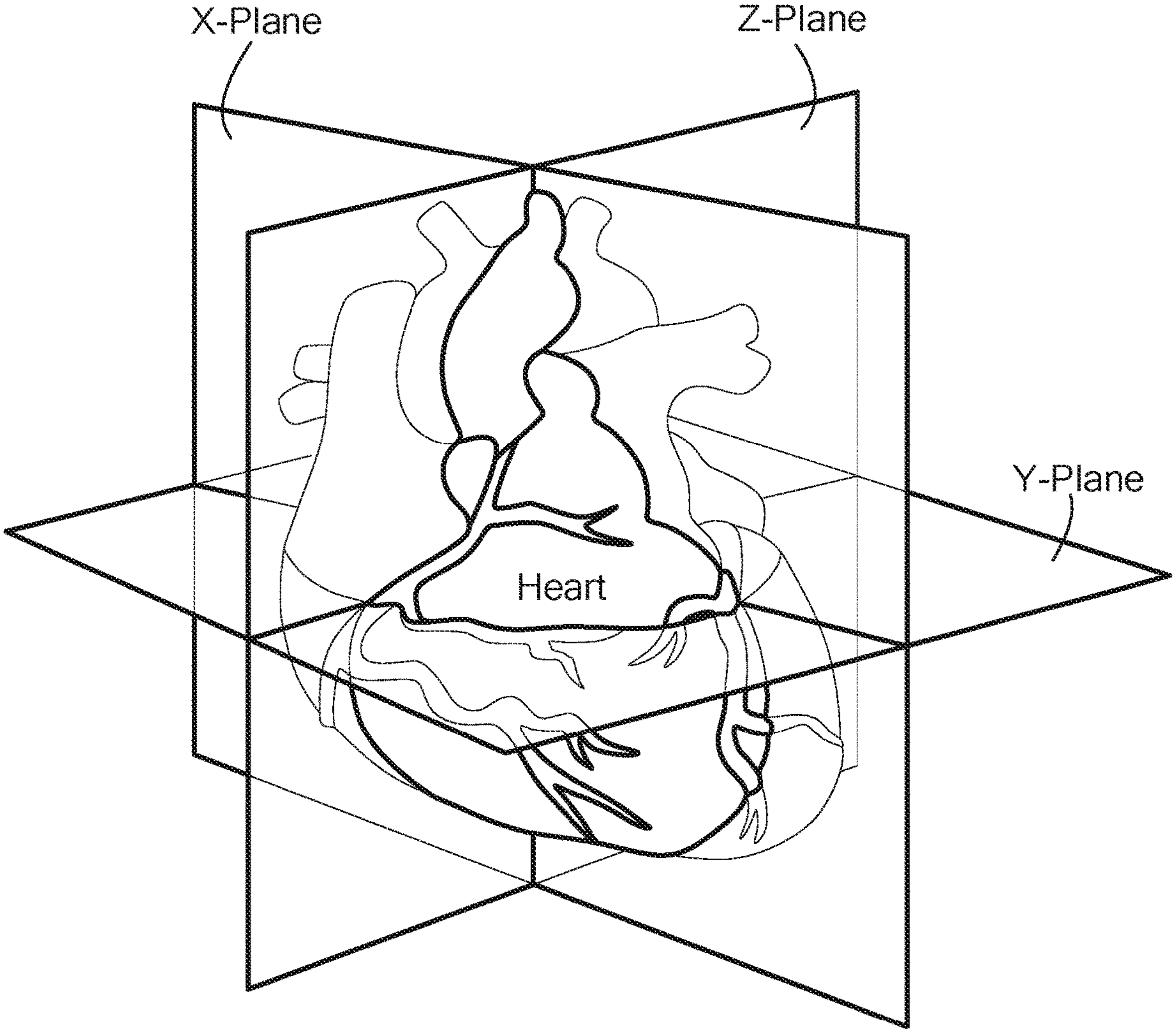
FIG. 4 shows a heart divided by imaginary X, Y, and Z planes.

As a non-limiting example, the navigation system 50 may be the LOCALISA™ system (Medtronic, Inc., Minneapolis, MN) or a similar system. The LOCALISA system, for example, is a system to localize a catheter or lead in the heart and to display the location graphically on a screen. The navigation system 50 may include an energy generator 52 that is configured to deliver alternating current (AC) energy from three AC sources at three separate frequencies in the 30 kHz region (for example, 30.27 kHz, 30.70 kHz, and 31.15 kHz) to external electrode patches 54. As is discussed below, however, such a system may be adapted or reconfigured to deliver the alternating current electricity at a single frequency to the external electrode patches 54. External electrode patches 54, which may be part of the navigation system 50, are used to orient the three current sources in the X, Y, and Z planes (shown in FIG. 4), although it will be understood that other system components may be used to generate the X-, Y-, and Z-plane current sources. In each plane, a voltage continuum is created from one electrode patch in a pair to the other of the pair such that a treatment device electrode 16 in that plane will act as the wiper of a potentiometer. The voltage measured by the treatment electrode(s) 16 and/or the mapping electrode(s) 36 will indicate the treatment device electrode's position in the plane. In previously known systems, filters are used to select one of the three frequencies and each plane's voltage can be obtained. Thus, the electrode's three-dimensional location can be determined. In an embodiment of the system disclosed herein, however, a single frequency may be time-division multiplexed into separate divisions for the X plane, Y plane, and Z plane, to determine the device's location.

Figure 5:
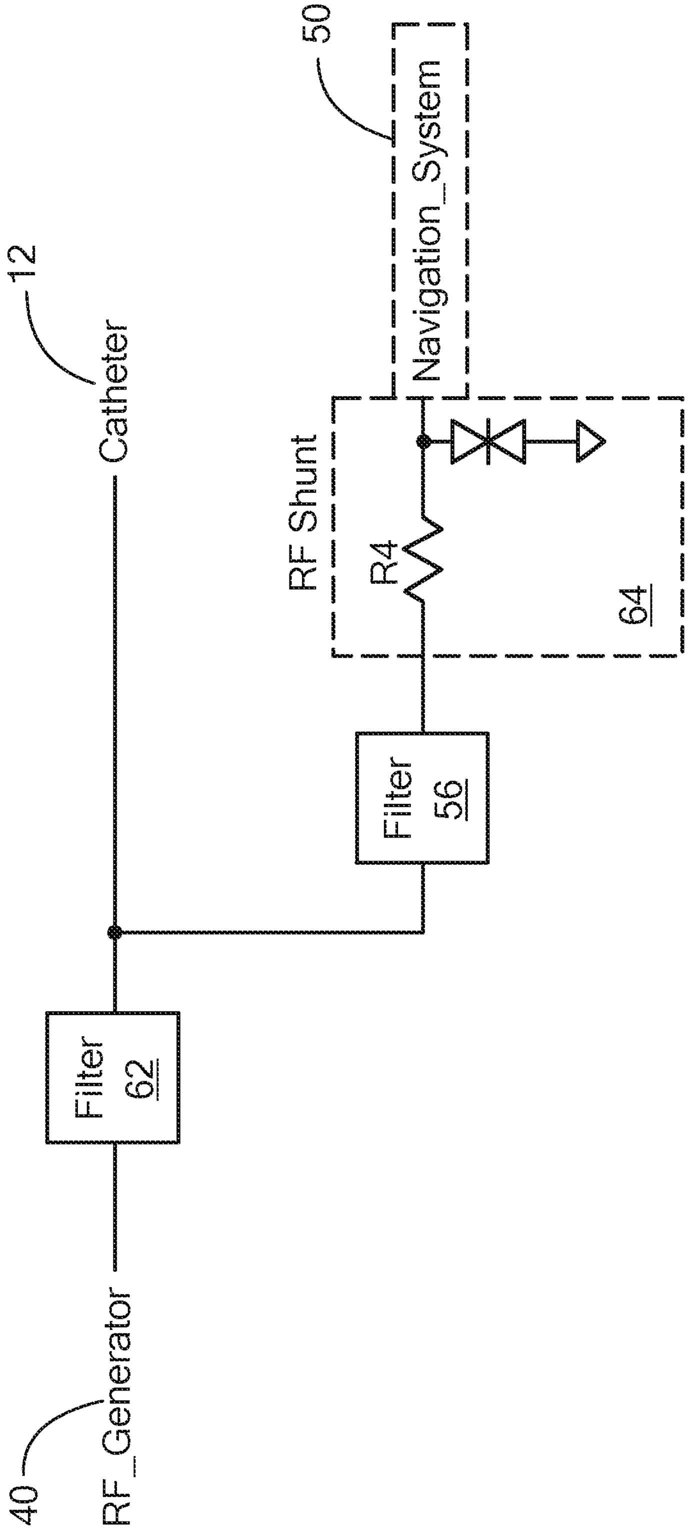
FIG. 5 shows a schematic diagram of a treatment system having filters.

To overcome the difficulties in using navigation systems during the delivery of energy, the system of FIGS. 1-3 may be configured for use with one of two methods. Although the system 10 is discussed as being configured for the delivery of RF energy, it will be understood that the system may be additionally or alternatively configured for the delivery of other energy modalities, including PFA. The first method involves the use of filtering the RF ablation signal from the RF navigation signal (as shown in FIG. 5). For example, a frequency-selective first filter 56 may be used that can be applied to the input 58 of the navigation system 50 equipment. The filter 56 may allow navigation energy to pass freely between the treatment device 12 and the navigation system 50, while presenting a high impedance and preventing ablation energy from entering and adversely affecting the navigation system 50. The filter 56 may be a band-reject filter that matches the frequency of the delivered ablation energy. As a non-limiting example, the frequency may be 460.8 kHz if the GENius® Generator is used. As a further non-limiting example, if the system is configured to deliver PFA energy, the frequency of the band-reject filter may be approximately 100 kHz. As yet another non-limiting example, if the system is configured to measure tissue contact impedance (that is, to sense electrode-tissue contact), the band-reject filter may have a first frequency of approximately 12.5 kHz and a second frequency of approximately 100 kHz. Additionally, a frequency-selective second filter 62 may be used at the energy generator 40 to prevent the RF ablation signal from interfering with the RF navigation signal. The filter 62 may be a band-reject filter that matches the frequency of the navigation system 50. As a non-limiting example, the frequency may be approximately 30 kHz if the LOCALISA system is used. A shunt 64 may be located between the first filter 56 and the navigation system 50 to protect the navigation system from ablation energy. Systems in which this method is used may not include the switching system 41 shown in FIGS. 1-3 and discussed in more detail below.

Figure 6:
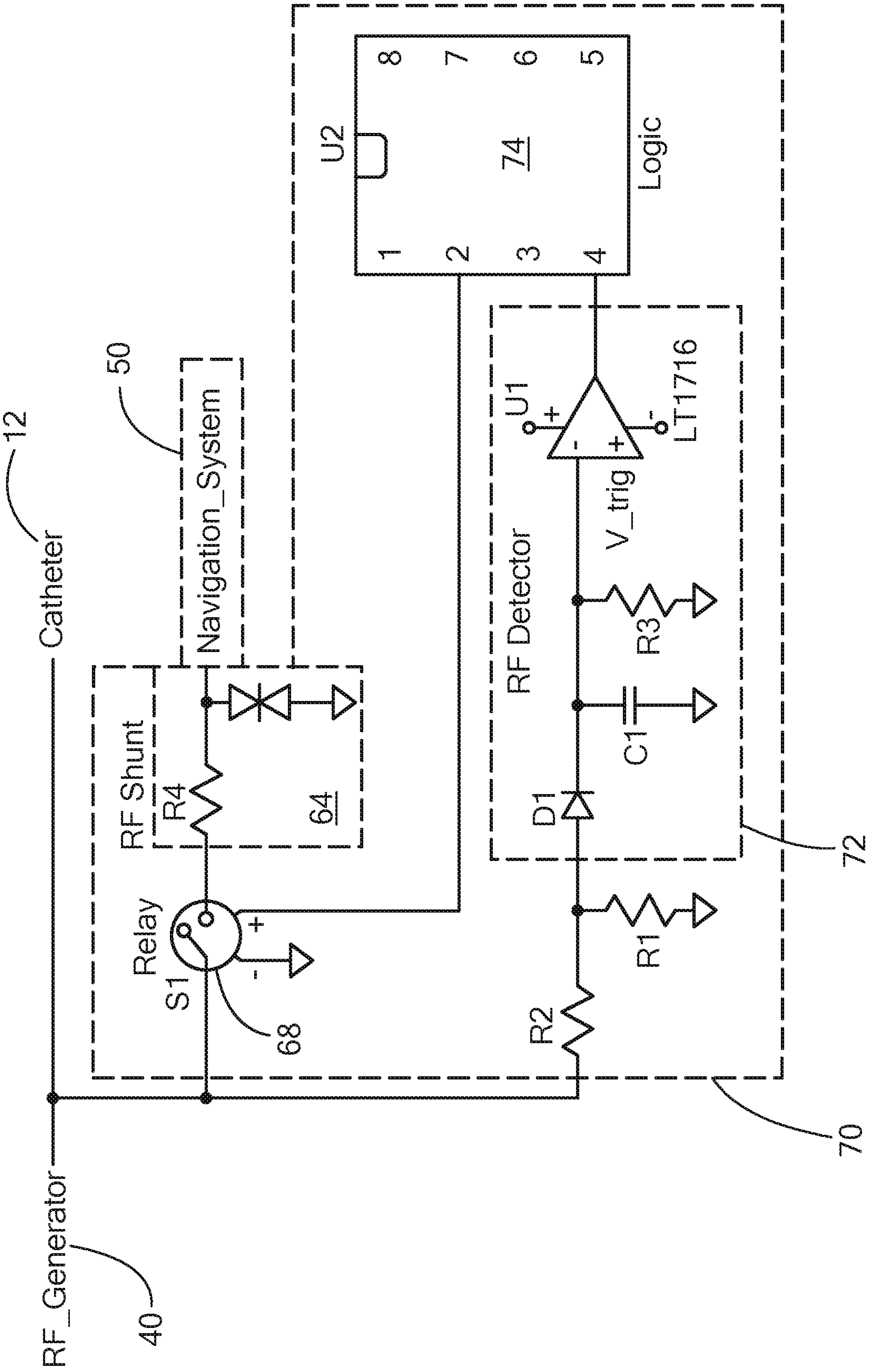
FIG. 6 shows a schematic diagram of a switching system for use in a treatment system.

The second method involves sequencing the delivery of ablation energy with the delivery of navigation energy. Referring now to FIG. 6, a schematic diagram of a switching system 41 is shown. A switch or relay 68 may be used that alternates the connection of the device electrode(s) 16 between the energy generator 40 and the navigation system 50. In this way, a portion of the overall therapy period may be assigned to the delivery of ablation energy (for example, pulsed RF or PFA energy) and the remainder of the overall therapy period may be assigned to the delivery of navigation energy. The switch 68 may be activated by the detection of ablation energy or by, for example, a microprocessor 70 that adjudicates and sequences the timing of the two periods. Additionally, although the switching system 41 is shown as being external to the console 18, this component may alternatively be located within the console 18 and/or integrated with the computer 42 and other components of the console 18.

In currently known systems, three AC sources are used at three separate frequencies in the 30 kHz region, with external electrode patches, for example, being used to orient the three current sources in the X, Y, and Z planes. In the system of FIGS. 1-3, however, a single frequency may be used that is time-division multiplexed into separate divisions for the X plane, Y plane, and Z plane. The single frequency may be any frequency, as long as the same frequency is delivered to all external electrode patches 54; however, frequencies between approximately 1 kHz and approximately 50 kHz have been used. Alternating current navigation energy may be delivered in these three planes by the external electrode patches 54 and the voltage signals may be measured by the mapping electrodes 36 and/or treatment electrodes 16 on the device. During each division, the voltage signals may be received by the processing unit 48 of the navigation system 50 from the mapping electrodes 36 and/or treatment electrodes 16 for that plane without the need for additional filtering. The processing unit 48 may then reassemble the voltage signals based on the timing.

Optionally, divisions may also be created following the three planes for sourcing AC to measure impedance (Z) and/or phase angle (θ) at multiple frequencies, such as a high frequency (HF) and a low frequency (LF), in both unipolar and bipolar delivery modes. Such measurements may be used to assess contact between treatment electrodes and tissue and/or cell health. For example, bipolar energy may be delivered between two intracardiac electrodes 16/36 and unipolar energy may be delivered between an intracardiac electrode 16/36 and an external electrode patch 54 or reference electrode. The low frequency and the high frequency may be delivered by the device 12 and the mapping electrodes 36 and/or the treatment electrodes 16 may measure the voltage that is produced. As a non-limiting example, the low frequency (LF) may be between approximately 5 kHz and approximately 25 kHz and the high frequency (HF) may be between approximately 80 kHz and approximately 120 kHz. However, the low frequency may be any frequency that allows good quality impedance measurements to be taken without stimulating the heart.

Figure 9:
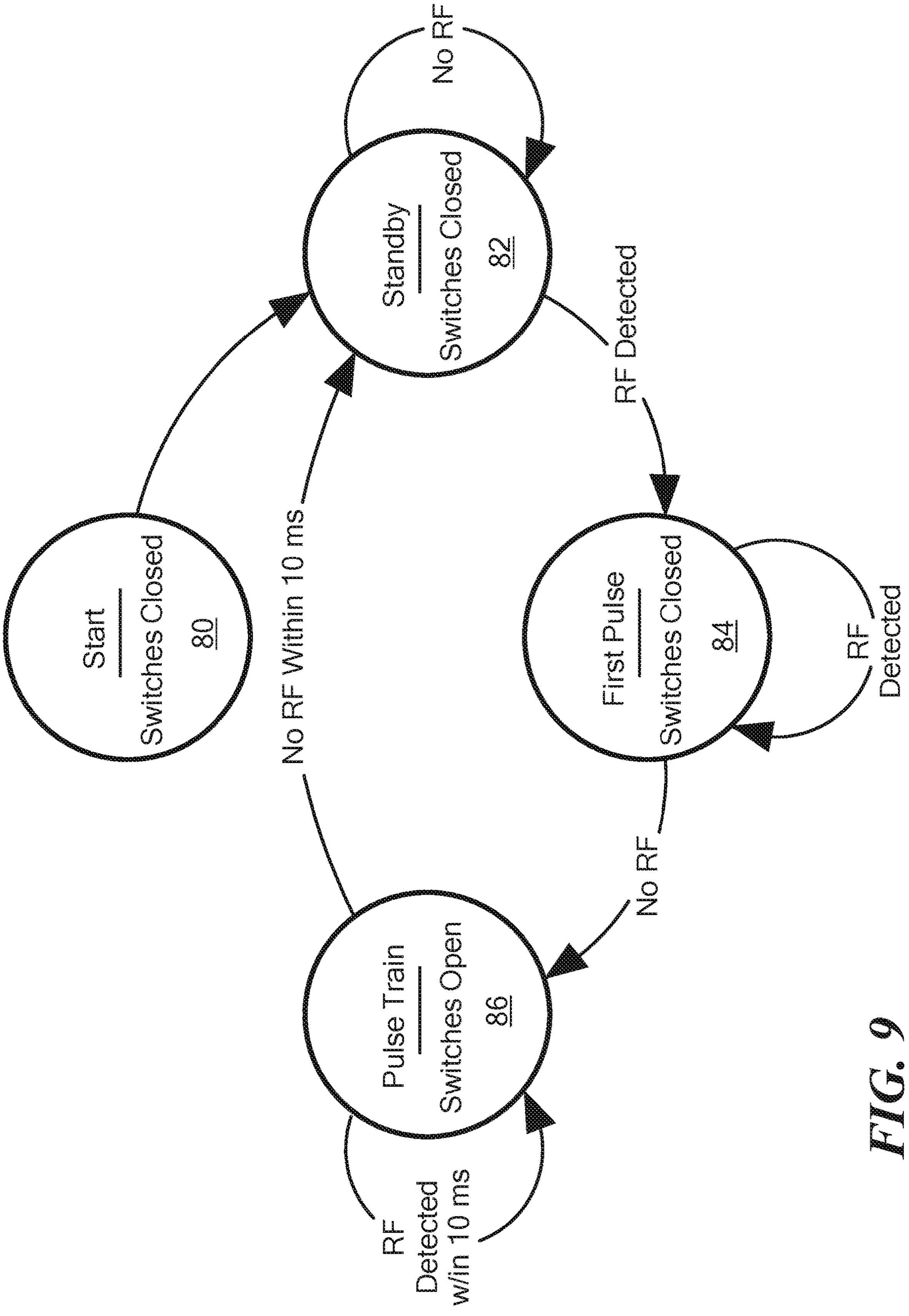
FIG. 9 shows a flowchart for switching behavior of the system.

Energy may be delivered to the target tissue by the medical device 12 in a duty cycle with an on period during which ablation energy is delivered and an off period during which device coordinates and other measurements may be taken. In this way, the navigation system 50 may be able to determine the location of the device 12 during the off periods of the treatment energy delivery by multiplexing position information taken in the X, Y, and Z planes during different off periods. Additionally, impedance and phase angle measurements, in unipolar and bipolar modes and at low and high frequencies, may each be taken during different off periods (as shown in FIG. 7; phase angle is not shown in the exemplary sequence of FIG. 7, but may nonetheless be included). Alternatively, impedance and phase angle measurements may be taken at the same time for each of the unipolar and bipolar modes and low and high frequencies (as shown in FIG. 9).

Treatment energy may be delivered according to a duty cycle. For example, each on period and immediately following off period (referred to as an on/off cycle in FIGS. 7 and 8) may together have a duration of approximately 8 msec, although it will be understood that the duration may be any amount of time suitable for the procedure and patient. RF treatment energy may be delivered during an on period by the one or more treatment electrodes 16 for a first period of time, such as approximately 1 msec. Then, during the off period, the X plane impedance measurements may be taken for a period of time (for example, approximately 7 msec). RF energy may be delivered again for between approximately 1 msec during the on period, and the Y plane impedance measurements may be taken during the off period (for example, between approximately 7 msec). This cycle may be repeated until all location, impedance, and phase angle measurements have been taken. If longer on/off cycles are used, the off period may be long enough to record more than one measurement. For example, the coordinates in the X, Y, and Z planes may all be recorded during a single longer off period.

Alternatively, pulsed field ablation (PFA) may be used to treat the tissue area instead of RF. As a non-limiting example, the same duty cycle configuration as described above for RF energy delivery may be used, but a PFA pulse train of between 15 μsec and 250 msec in duration may be delivered during the on periods of the duty cycle, between impedance measurements during the off periods of the duty cycle. As a non-limiting example, individual pulses may be 5 μsec in duration with an off period of at least 5 μsec between pulses, and each pulse train may include 60 to 120 pulses. One or more pulse trains may be delivered during the treatment procedure. The impedance measurements may be taken between individual pulses or between pulse trains.

As shown in FIG. 6, the switching system 41 may include the switch 68, an energy detector 72 that detects when ablation energy is present (for example, the energy detector 72 may be an RF detector that detects when RF ablation energy is being delivered), a logic apparatus 74 that controls the switch 68 based on the RF detector's information, and a shunt 64 that protects the navigation system 50 in a period of time after the delivery of ablation energy starts but before the switch 68 has engaged. Although the energy detector 72 may be referred to herein as a RF energy detector, it will be understood that the detector 72 may also be configured to detect other types of energy, such as pulsed electric field energy for PFA procedures. The switching system 41 may switch between ablation energy delivery and obtaining coordinates of the device 12 based on either the detection of ablation energy by the energy detector 72, as shown and described in FIG. 9, or based on a known duty cycle.

Referring now to FIG. 9, a flowchart for the switching system behavior is shown. Although the delivery and detection of RF energy is discussed here, it will be understood that phased RF energy, pulsed electric field energy, and/or other energy modalities may be used. When the switch 68 is open, energy may flow from the RF energy generator 40 to the treatment device 12 without affecting the navigation system 50. When the switch 68 is closed, the treatment device 12 is in electrical communication with the navigation system 50 and does not deliver RF ablation energy. At the start of the cycle (80), the switch 68 may be closed and the location of the treatment device 12 may be monitored by the navigation system 50. If no RF energy is detected by the energy detector 72, the system 41 may enter or remain in a standby mode, in which the switch 68 remains closed (82). The first time the energy detector 72 detects RF energy, the switch 68 may remain closed but the switching system 41 may recognize commencement of an ablation or treatment cycle (84). After a period of no RF energy being detected, the switch 68 may open to disconnect the navigation system 50 from the treatment device 12 in preparation for the delivery of RF energy (86), such as RF ablation energy. The energy generator 40 may transmit a burst of RF ablation energy (or, for example, a pulse train of pulsed electric field energy) to the treatment device 12 and the switch 68 may remain open despite periods of no RF energy being detected, as long as the periods of RF energy delivery are within, for example, 10 msec of each other (indicating the delivery of ablation energy). If a period of, for example, 10 msec elapses without the energy detector 72 detecting RF energy, this may indicate that the delivery of RF ablation energy has ended. In this case, the switching system 41 may return to the standby mode with the switch 68 closed.

Using the switching system behavior shown in FIG. 7, coordinates of the treatment device 12 may be recorded during the periods of time between the duty cycles of RF ablation energy. For example, the switch 68 may be open when RF ablation energy is delivered. After the delivery of a burst of RF ablation energy (or, for example, a pulse train of pulsed electric field energy), the switching system 41 may measure the X-plane coordinates of the treatment device 12 for approximately 2-4 msec. Another burst of RF ablation energy may be delivered, after which the switching system 41 may measure the Y-plane coordinates of the treatment device 12 for approximately 2-4 msec. Finally, another burst of RF ablation energy may be delivered, after which the switching system 41 may measure the Z-plane coordinates of the treatment device 12 for approximately 2-4 msec. This sequence may be repeated as many times as desired throughout the ablation procedure.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of determining a location of a treatment device during an ablation procedure within a patient, the method comprising:
- delivering ablation energy from an ablation electrode of the treatment device to an area of tissue;
- delivering navigation energy to a plurality of external patch electrodes from a plurality of navigation energy sources, the navigation energy delivered by each of the plurality of navigation energy sources being a same frequency;
- transmitting a plurality of voltage signals from a mapping electrode of the medical device to a processing unit, the processing unit time-division multiplexing the voltage signals, wherein the processing unit time-division multiplexes the voltage signals in each of a first plane, a second plane, and a third plane; and
- determining a location of the medical device within a patient based on the time-division multiplexed voltage signals.

2. The method of claim 1, wherein the frequency is between 5 kHz and 25 kHz, the method further comprising:
- transmitting a plurality of impedance signals from the mapping electrode of the medical device to the processing unit when the navigation energy is delivered in unipolar mode, the processing unit time-division multiplexing the impedance signals; and
- transmitting a plurality of impedance signals from the mapping electrode of the medical device to the processing unit when the navigation energy is delivered in bipolar mode, the processing unit time-division multiplexing the impedance signals.

3. The method of claim 1, wherein the frequency is a between 80 kHz and 120 kHz, the method further comprising:
- transmitting a plurality of impedance signals from the mapping electrode of the medical device to the processing unit when the navigation energy is delivered in unipolar mode, the processing unit time-division multiplexing the impedance signals; and
- transmitting a plurality of impedance signals from the mapping electrode of the medical device to the processing unit when the navigation energy is delivered in bipolar mode, the processing unit time-division multiplexing the impedance signals.

4. The method of claim 1, wherein delivering ablation energy from the ablation electrode of the treatment device is during an on period and the delivering of ablation energy stops during an off period.

5. The method of claim 4, wherein the navigation energy sources are alternating current sources, and wherein the alternating current sources are configured to deliver alternating current electricity to each of the external patch electrodes at the same frequency.

6. The method of claim 1, wherein the navigation energy sources are alternating current sources, and wherein the alternating current sources are configured to deliver alternating current electricity to each of the external patch electrodes at the same frequency.

7. The method of claim 1, wherein the delivered ablation energy is pulsed electric field energy.

8. A method of determining a location of a treatment device during an ablation procedure within a patient, the method comprising:
- delivering ablation energy from an energy generator to an ablation electrode of the treatment device to an area of tissue;
- delivering navigation energy to a plurality of external patch electrodes from a plurality of navigation energy sources, the navigation energy delivered by each of the plurality of navigation energy sources being a same frequency;
- filtering the delivery of the ablation energy and the delivery of navigation energy using a first filter that is applied to an input of the navigation energy sources, the first filter allowing navigation energy to pass between the treatment device and the plurality of navigation energy sources while presenting a high impedance and preventing the ablation energy from entering the plurality of external patch electrodes;
- transmitting a plurality of voltage signals from a mapping electrode of the medical device to a processing unit, the processing unit time-division multiplexing the voltage signals, wherein the processing unit time-division multiplexes the voltage signals in each of a first plane, a second plane, and a third plane; and determining a location of the medical device within a patient based on the time-division multiplexed voltage signals.

9. The method of claim 8, wherein the plurality of navigation energy sources are three alternating current energy sources that deliver energy at three separate frequencies.

10. The method of claim 9, wherein the three separate frequencies are each at least 30 kHz, the three separate frequencies being delivered to the external patch electrodes.

11. The method of claim 8, wherein the first filter is a band-reject filter that matches the frequency of the delivered ablation energy.

12. The method of claim 11, wherein the band-reject filter matches at least one of the following frequencies 460.8 kHz and 100 kHz.

13. The method of claim 8, further comprising:

filtering the delivery of ablation energy from the energy generator with a second filter that is at the energy generator to prevent the ablation energy from interfering with the navigation energy.

14. The method of claim 13, wherein the second filter is a band-reject filter that matches the frequency of the delivered navigation energy.

* * * * *